(12) United States Patent
Cotereau

(10) Patent No.: US 11,224,633 B2
(45) Date of Patent: Jan. 18, 2022

(54) KIT FOR TREATING SEPSIS AND/OR ANY SYSTEMIC (SIRS) OR DAMAGING CELLULAR HYPERINFLAMMATION

(71) Applicant: SERENITE-FORCEVILLE, Suresnes (FR)

(72) Inventor: Vincent Cotereau, Boulogne-Billancourt (FR)

(73) Assignee: SERENITE-FORCEVILLE, Suresnes (FR)

(*) Notice: Subject to any disclaimer, the term of this patent is extended or adjusted under 35 U.S.C. 154(b) by 0 days.

(21) Appl. No.: 15/738,934

(22) PCT Filed: Jun. 24, 2016

(86) PCT No.: PCT/FR2016/051569
§ 371 (c)(1),
(2) Date: Dec. 21, 2017

(87) PCT Pub. No.: WO2016/207577
PCT Pub. Date: Dec. 29, 2016

(65) Prior Publication Data
US 2018/0185443 A1    Jul. 5, 2018

(30) Foreign Application Priority Data
Jun. 25, 2015 (FR) ..................................... 1555893

(51) Int. Cl.
| | | |
|---|---|---|
| *A61K 31/385* | (2006.01) | |
| *A61K 31/18* | (2006.01) | |
| *A61K 33/04* | (2006.01) | |
| *A61K 31/095* | (2006.01) | |
| *A61P 35/00* | (2006.01) | |
| *A01N 59/02* | (2006.01) | |
| *A61K 38/17* | (2006.01) | |
| *A61P 31/00* | (2006.01) | |
| *A61P 37/06* | (2006.01) | |
| *A61K 45/06* | (2006.01) | |

(52) U.S. Cl.
CPC .............. *A61K 38/17* (2013.01); *A61K 33/04* (2013.01); *A61K 45/06* (2013.01); *A61P 31/00* (2018.01); *A61P 37/06* (2018.01); *G01N 2800/26* (2013.01)

(58) Field of Classification Search
CPC .. A61K 33/04; A61K 2300/00; A61K 31/095; G01N 2800/26; A61P 31/00; A61P 35/02; A61P 35/00; A61P 43/00; A61P 37/00; A61P 29/00; A01N 59/02
See application file for complete search history.

(56) References Cited

U.S. PATENT DOCUMENTS

| | | | |
|---|---|---|---|
| 6,656,509 B1 * | 12/2003 | Stiefel ................. | A61K 31/095 424/617 |
| 7,635,491 B2 | 12/2009 | Forceville | |
| 9,295,775 B2 | 3/2016 | Duffour et al. | |
| 2004/0242996 A1 | 12/2004 | Trombley | |
| 2005/0163862 A1 * | 7/2005 | Forceville .............. | A61K 33/04 424/618 |
| 2011/0183911 A1 * | 7/2011 | Kawamura ........ | A61K 38/1709 514/17.7 |
| 2015/0147276 A1 * | 5/2015 | Ingber ................. | A61K 38/482 424/9.5 |

FOREIGN PATENT DOCUMENTS

| | | |
|---|---|---|
| EP | 1393078 A1 | 3/2004 |
| EP | 1713528 A2 | 10/2006 |
| EP | 2298382 A1 | 3/2011 |
| EP | 2477677 A1 | 7/2012 |
| FR | 2782642 A1 | 3/2000 |
| JP | 2004-182683 A | 7/2004 |
| WO | 02-093175 A1 | 11/2002 |
| WO | 2005-079886 A2 | 9/2005 |
| WO | 2005-104687 A2 | 11/2005 |
| WO | 2011-033440 A1 | 3/2011 |

OTHER PUBLICATIONS

English machine translation of JP 2004182683 A (machine translated on Aug. 5, 2019 and originally published in Japanese on Jul. 2, 2004) (7 pages) (Year: 2004).*
Gründling et al., "Acute high-dose sodium selenite administration improves intestinal microcirculation without affecting cytokine release in experimental endotoxemia," Journal of Trace Elements in Medicine and Biology, 2009;23(2):138-43.
Alhazzani, Waleed et al., "The effect of selenium therapy on mortality in patients with sepsis syndrome: a systematic review and meta-analysis of randomized controlled trials," Crit Care Med. Jun. 2013;41(6):1555-64.
Angstwurm, MW et al., "Selenium in Intensive Care (SIC) study: results of a prospective randomized, placebo-controlled, multiple-center study in patients with severe systemic inflammatory response syndrome, sepsis, and septic shock," Crit Care Med. Jan. 2007;35(1):118-26.
Casaer, MP and Van Den Berghe, "Nutrition in the acute phase of critical illness." N Engl J Med. Mar. 27, 2014;370(13):1227-36.
Dellinger, RP et al., "Surviving sepsis campaign: international guidelines for management of severe sepsis and septic shock: 2012," Crit Care Med. Feb. 2013;41(2):580-637.

(Continued)

*Primary Examiner* — Tracy Liu
(74) *Attorney, Agent, or Firm* — Nixon & Vanderhye

(57) ABSTRACT

Disclosed is a kit including a first container including a composition including at least one antioxidant selenoprotein and at least one second container including at least one composition including at least one oxidant selenocompound. Also disclosed is a method of administration that allows to administer effective and cytotoxic doses of selenocompounds, allowing the inhibition of the hyper-activation of phagocytes and in particular of circulating immature neutrophils and directly and indirectly protects endothelial cells, in particular for the treatment of sepsis, SIRS and leukemia. Further disclosed is an administration device adapted to the administration method.

15 Claims, 2 Drawing Sheets

(56) References Cited

OTHER PUBLICATIONS

Dodge, JT et al., "The preparation and chemical characteristics of hemoglobin-free ghosts of human erythrocyte," Arch Biochem Biophys. Jan. 1963;100:119-30.

Forceville, X et al., "Selenium, systemic immune response syndrome, sepsis, and outcome in critically ill patients." Crit Care Med. Sep. 1998;26(9):1536-44.

Forceville, X, "Effects of high doses of selenium, as sodium selenite, in septic shock patients a placebo-controlled, randomized, double-blind, multi-center phase II study." Journal of Trace Elements in Medicine and Biology 21 (2007) S1, pp. 62-65.

Forceville, X "The effect of selenium therapy on mortality in patients with sepsis syndrome: simple selenium supplementation or real (5 H2O)—Na2SeO3 pharmacological effect?*" Crit Care Med. Jun. 2013;41(6):1591-2.

Forceville, X et al., "Elements of margin of safety, toxicity and action of sodium selenite in a lipopolysaccharide rat model." J Trace Elem Med Biol. Jul. 2014;28(3):303-10.

Heyland, DK, "Selenium supplementation in critically ill patients: can too much of a good thing be a bad thing?" Crit Care. 2007;11(4):153.

Huang, Z et al., "The role of selenium in inflammation and immunity: from molecular mechanisms to therapeutic opportunities." Antioxid Redox Signal. Apr. 1, 2012;16(7):705-43.

Kelly, C et al., "Targeted liposomal drug delivery to monocytes and macrophages," J Drug Deliv. 2011;2011:727241.

Manzanares, W et al., "Pharmaconutrition with selenium in critically ill patients: what do we know?" Nutr Clin Pract. Feb. 2015;30(1):34-43.

Misra, S et al., "Redox-active selenium compounds—from toxicity and cell death to cancer treatment." Nutrients. May 13, 2015;7(5):3536-56.

Nutall, KL, "Evaluating Selenium Poisoning." Ann Clin Lab Sci. 2006 Autumn;36(4):409-20.

Shaillender, M et al., "Layer-by-layer microcapsules templated on erythrocyte ghost carriers." International Journal of Pharmaceutics 415 (2011) 211-217.

Singer, P et al., "ESPEN Guidelines on Parenteral Nutrition: intensive care." Clin Nutr. Aug. 2009;28(4):387-400.

Singer, M et al., "The Third International Consensus Definitions for Sepsis and Septic Shock (Sepsis-3)." JAMA. 2016;315(8):801-810.

Stewart, MS et al., "Selenium compounds have disparate abilities to impose oxidative stress and induce apoptosis." Free Radic Biol Med. Jan. 1999;26(1-2):42-8.

Vergaro, V et al., "Drug-loaded polyelectrolyte microcapsules for sustained targeting of cancer cells." Adv Drug Deliv Rev. Aug. 14, 2011;63(9):847-64.

Wang, Z et al., "A large-bolus injection, but not continuous infusion of sodium selenite improves outcome in peritonitis." Shock Aug. 2009;32(2):140-6.

Brodin, O et al., "Pharmacokinetics and Toxicity of Sodium Selenite in the Treatment of Patients with Carcinoma in a Phase I Clinical Trial: The SECAR Study." Nutrients 2015;7(6):4978-4994.

Sakr, Y et al., "Adjuvant selenium supplementation in the form of sodium selenite in postoperative critically ill patients with severe sepsis." Crit Care 2014;18(2):R68.

International Search Report, dated Nov. 23, 2016, from corresponding PCT application No. PCT/FR2016/051569.

Dietary Reference Intakes for Vitamin C, Vitamin E, Selenium, and Carotenoids: A Report of the Panel on Dietary Antioxidants and Related Compounds, Subcommittees on Upper Reference Levels of Nutrients and Interpretation and Uses of Dietary Reference Intakes, and the Standing Committee on the Scientific Evaluation of Dietary Reference Intakes Food and Nutrition Board Institute of Medicine, 2000.

Panel on Micronutrients, Subcommittees on Upper Reference Levels of Nutrients and of Interpretation and Use of Dietary Reference Intakes, and the Standing Committee on the Scientific Evaluation of Dietary Reference Intakes, "Dietary Reference Intakes for Vitamin A, Vitamin K, Arsenic, Boron, Chromium, Copper, Iodine, Iron, Manganese, Molybdenum, Nickel, Silicon, Vanadium, and Zinc," 2001.

Sener, G. et al., "Protective effect of beta-glucan against oxidative organ injury in a rat model of sepsis," International Immunopharmacology 5 (2005) 1387-1396.

\* cited by examiner

KIT FOR TREATING SEPSIS AND/OR ANY SYSTEMIC (SIRS) OR DAMAGING CELLULAR HYPERINFLAMMATION

FIELD OF INVENTION

The present invention relates particularly to the treatment of sepsis, of systemic inflammatory response syndrome (SIRS) and more particularly of septic shock and of SIRS conditions resulting in similar situations requiring the use of catecholamines after filling or during the fast filling phase in the case of very sudden aggravation. The present invention also relates to a treatment of leukemia (for circulating elements). In particular, the present invention relates to an association in a kit of a selenoprotein and a selenocompound for the treatment of these syndromes and diseases. The present invention also relates to an administration method that can be used to administer effective doses of selenocompounds toxic for circulating hyperactive cells and pathogens (bacteria, virus, fungi and parasites) but beneficial as a whole for the complete organism. Finally, another aspect of the invention relates to an administration device.

BACKGROUND OF INVENTION

Sepsis corresponds to an excessive systemic inflammatory response of the organism usually in reaction to a bacterial infection, but also to a parasite, viral or fungal infection. In the current state of the art sepsis is a syndrome and not a disease. Severe sepsis is defined by the presence of one or several dysfunctions or failures of organs and of signs of peripheral hypo-perfusion, while septic shock is defined by the presence of a persistent hypotension despite adequate filling, usually associated with multiple organ failures. Adequate generally means filling of 20 to 30 mg/kg. In both cases, an excessive or badly adapted complex response of the organism requires the use of substitution of major functions in resuscitation to prevent death. This complex deployment of assistance to major functions allows persons to survive sepsis, who would not survive otherwise; however, despite these expensive substitutions, the mortality rates of these patients, 28 days after the beginning of the episode, are about 20 to 30%, and 40 to 50%, respectively. Furthermore, the number of beds in resuscitation services for their efficient treatment is limited. Sepsis thus results in a very significant number of deaths, slightly higher than that due to myocardial infarction, and is the leading causing of death in hospitals and accounts for more than 5% of hospital expenses (0.5% of the GDP). It is one of the leading causes of death in the world and would be the leading cause in the case of a pandemic in which resuscitation services were completely overloaded. It corresponds to one of the main causes of health expenses in current practice around the world. Furthermore, it would be an important cause of death in the case of a pandemic situation—sepsis is the origin of deaths for example in the case of plague epidemics —, disasters (associated with crush injuries), bioterrorism or war. In the latter case, it would easily be associated with another cause of the systemic inflammation caused by extensive burns, which would account for more than 30% of all victims. Acute inflammation is also a major event in irradiation victims who do not die immediately.

At the present time, treatment of this medical emergency consists in the administration of antibiotics within one hour, associated with filling, oxygenation, the introduction of catecholamines and management in resuscitation services in the absence of specific treatment. Furthermore, a low dose of corticoids may be administered to the patient but this remains very controversial and has limited—if any—efficiency. Worldwide recommendations have been produced in the framework of the surviving sepsis campaign, cooperative work done worldwide including the main resuscitation companies, including American and European companies. Nevertheless, at the present time there is no specific treatment for this excessive defense reaction of the organism, and most proposed treatments are attempts to allow the organism to survive this self-aggression situation by implementing the most judicious possible life-support while waiting for the end of this reaction, having treated the origin of what triggered it (activation of toll-receptors), infectious in the case of sepsis (PAMPS), cell damage in the case of systemic acute inflammatory syndromes (DAMPS).

At the microcirculation level, the interaction of phagocyte cells and the endothelium, succeeding the very fast alert of cells of the secondary innate response to activation of Toll receptors, participates in the modification of the endothelium (flip-flap) changing from a non-adherent, non-inflammatory and non-coagulating endothelium to an adherent, inflammatory and coagulating endothelium then damaged with abrasion of the endothelium surface layer (ESL), formation of nitro-oxygenated reactive derivative—such as peroxynitrite by the joint action of adherent granulocytes (emission of superoxide anion) and activated endothelial cells (emission of NO), emission of microparticles, and opening of tight junctions and distress of the endothelium. This dysfunction of the microcirculation and this distress of the endothelium are considered as one of the elements or the major element in the occurrence of multiple organ failures secondary to severe sepsis and to septic shock. These multiple organ failures can lead to death despite life-support in resuscitation services that enables patients who would otherwise have died to survive temporarily or not, and lead to death in the absence of this resuscitation care. It can be considered (mathematical model applied to biology) that this situation was a chaos situation.

The objective of resuscitation is then to bring the subject, once the acute episode has passed, to the homeostasis attractor by progressively liberating survival attractors related to life-support. This hyper-inflammatory state usually leads to acquired immunodeficiency that will be the ground for new infections, possibly with pathogens not dangerous in a non-immunodepressed subject and that can lead to another sepsis reaction. There is then a strong risk of going from septic shock to septic shock until the subject becomes exhausted in a sequence of stagnation and major malnutrition usually leading to a therapeutic limitation in an out-of-control situation in which it no longer seems possible to return to a situation without life-support, corresponding to obstinacy.

Reactive oxygen derivatives (oxidative metabolism (respiratory burst) of granulocytes, hyperactivation of endothelial cells with the synthesis of NO, ischemia-reperfusion phenomena and mitochondrial distress) generated by the struggle against infectious agents play a major role in endothelial dysfunction, the first step towards multiple organ failures and death. Selenium is a bivalent atom in physiopathology. Physicochemically, it is in column VI which is the column of oxygen (chalcogens chemical family). Indeed, chemically and biochemically, small selenocompounds are often toxic oxidizing molecules.

Thus, sodium selenite is one of the most toxic selenocompounds and its toxicity is similar to the toxicity of arsenic salts. A concentration of 10 µmol/L leads to cell destruction for detached cells (Stewart M S, Free Radic Biol Med. 1999 January; 26(1-2):42-8). A selenium concentration of 18 µmol/L is observed in the case of lethal intoxication (Nuttall K L, Ann Clin Lab Sci. 2006 Autumn; 36(4):409-20). The lethal dose in man would appear to be of the order of 1.5 to 3 mg/kg. Sodium selenite will react preferentially with disulfide bridges. Its toxicity is higher on free cells than on cell layers, and also much higher on hyper-activated cells than on quiescent cells. In vitro, its cytotoxic activity particularly on cancer cells has been demonstrated for concentrations of selenium above 2 to 5 µmol/L in the form of sodium selenite. The toxicity of sodium selenite appears to act principally at the mitochondria level particularly in cells in hyperactivity.

Incorporated into selenoproteins, selenium—like that included in the sodium selenite molecule—enables these proteins to be a key element in the antioxidant defense in mammals. Consequently, cases of acute poisoning by selenocompounds are fully reversible if they are not fatal, since once incorporated into these selenoproteins, selenium has an antioxidant action opposite to that of oxidizing selenocompounds like selenite. In order to improve their antioxidant defense (and their regulation of the intra-cellular redox potential modulating all cell activity), mammals and birds have acquired a particular amino acid, selenocysteine, in which selenium replaces sulfur in cysteine. This replacement is genetically controlled with the modification of the significance of the UGA stop codon due to the presence of an adjacent structure and requires energy in the form of ATP. The presence of this amino acid at the active site of selenoenyzmes will enable these enzymes to have a faster and more robust antioxidant action than their iron precursors and replacement of selenocysteine by cysteine at the active site reduces the efficiency of these enzymes by a factor of 1000. Selenoproteins are major antioxidant enzymes in mammals. A shortage of selenium is fatal in man and the knock-out model for selenocysteine is fatal.

At the plasma level, there are two selenoproteins, namely selenoprotein-P, a protein that is highly conserved across species and an exception among selenoenzymes due to the fact that it comprises 9 selenocysteine amino acids (while the others only have one selenocysteine amino acid), and plasma glutathione peroxidase. Selenoprotein-P (Sel-P) accounts for 60% of plasma selenium. It transports biologically active selenium (selenocysteine) between the liver and tissues and participates directly in antioxidant protection of the endothelium by an enzymatic action, probably detoxifying, of the peroxynitrite ion. It has been shown that it plays a role in membrane stabilization limiting the emission of microparticles.

Due to apprehension of the toxicity of sodium selenite, this selenite was administered continuously or with boluses over 30 minutes as described in Angstwurm M W, (Crit Care Med. 2007 January; 35(1):118-26) who observes a tendency towards a decrease in mortality with an administration of 1000 µg of selenium in the form of sodium selenite (14 µg/kg) followed by an administration of the same dose continuously over 24 h, continued for 15 days, but whose results have not yet been reproduced (Angstwurm M W, Crit Care Med. 2007 January; 35(1):118-26). The maximum dose of 1000 µg/day is recommended by Heyland D K (Crit Care. 2007; 11(4):153), since a dose of 4000 µg/day (55 µg/kg) administered continuously did not have a beneficial effect, in his opinion due to negative effects. The bolus administration of 2000 µg (80 µg/kg) in sheep achieves positive effects, contrary to the administration of the same dose continuously, nevertheless it cannot be used to reach a conclusion about the advantage of bolus administration (Wang Z et al. Shock. 2009 August; 32(2):140-6). In fact, the advantage of this bolus administration remains very debatable (Alhazzani, W. et al. Crit Care Med. 2013 June; 41(6):1555-64). At the present time, the recommendations of the European Nutrition Society (ESPEN) are to not exceed 750 to 1000 µg/day due to risks of toxicity (Singer P et al. Clin Nutr. 2009 August; 28(4):387-400), this corresponds to the NOAEL No Adverse Effect Level determined in nutrition (800 µg, which is 11 µg/kg per day). On its part, the American Nutrition Society, ASPEN, recommends an optimum input between 500 and 750 µg/day. Considering the different study results, the benefits of administration of selenium in resuscitation patients in sepsis are not recommended in Dellinger R P et al. Crit Care Med. 2013 June; 41(2):580-637) nor in Casaer M P et al. (N Engl J Med. 2014 Mar. 27; 370(13):1227-36).

However, the Applicant remains convinced that the administration of compounds containing selenium (or selenite) is a suitable response to manage toxic circulating elements in the case of sepsis and leukemia.

In this context, the Applicant considered how the administration of compounds containing selenium could be optimized, while protecting the organism from their toxic effects. To the Applicant's knowledge, there is currently no solution to this technical problem. And in any case, there is a very strong need for means of significantly reducing the high death rate in patients suffering from sepsis and leukemia.

SUMMARY

The purpose of the invention is to disclose a solution to this technical problem and to disclose a treatment that targets phagocytes, in particular neutrophils, by a two-step administration of compounds, preferably selenocompounds, of different natures, firstly an antioxidant protein, preferably a selenoprotein, and then secondly an oxidant compound, preferably a selenocompound, in ultra-fast administration (also called flash administration), and preferably in a few repeated flashes, and not in bolus administration.

The invention directly and indirectly protects endothelial cells, limits adhesion of neutrophils to endothelial cells while inhibiting the hyper-activation of phagocytes and particularly immature circulating neutrophils. It can also participate in antibiotherapy, when the subject receives an antibiotherapy, by a cytotoxic effect on circulating pathogenic agents, including when the subject is resistant to the antibiotherapy.

Definitions

In the present invention, the following terms have the following meanings:

"Treatment", "treat" or "relieve" are terms related to the therapeutic treatment, and mean delaying the installation of a syndrome or a disease, stopping the syndrome or the disease, or causing regression of the syndrome or the disease. In one embodiment, the syndrome is sepsis; therefore, the subjects concerned by the invention include subjects in the initial phase of sepsis, notably diagnosed by a reduction in the circulating selenoprotein-P or by any other biomarker of sepsis, and/or subjects in whom sepsis has already been diagnosed or proven. A subject is considered to be effectively treated for sepsis if he or she or it shows an observable and/or measurable reduction in the production of nitrogen oxide and/or lactate, and/or a significant reduction in the death rate and/or a reduction in the severity of organ failures (that can be measured by the SOFA score). These parameters for evaluation of an effective treatment can easily be measured by routine procedures known to the physician. In another embodiment, the disease is a cancer, circulating or solid tumor; therefore, the subjects concerned by the invention include subjects suffering from a cancer.

An "excipient" denotes, according to the present invention, any substance other than the active substance present in a composition conferring properties of stability, form (liquid, solid, gel, etc., depending on the administration method), taste, dissolution (for example targeted dissolution in the stomach or digestive tract), color, etc. A "pharmaceutically acceptable excipient" more specifically denotes an excipient that does not induce an allergic or unwanted reaction during its administration. This definition includes particularly all of the pharmaceutically acceptable solvents and dispersion media.

The "effective amount" (or "therapeutically effective amount") for the treatment of sepsis refers to a necessary or sufficient amount to (1) delay or stop a sepsis, (2) make improvements to a sepsis, (3) reduce the severity or the incidence of a sepsis, (4) stop or treat a sepsis, without causing any secondary effects significant and harmful to the subject; concerning the administration of the antioxidant protein, preferably a selenoprotein, administered first according to the invention, the effective amount is the amount capable of protecting the endothelium against inflammation and hyper-oxidation induced by the sepsis, but also against the toxicity of sodium selenite or another oxidant selenocompound susceptible to be administered at a later time; an effective amount of antioxidant protein, preferably a selenoprotein, can be administered before the appearance of the sepsis, for prophylactic or preventive action; alternatively or additionally, an effective amount of selenoprotein can be administered after the appearance of the sepsis, for a therapeutic action; concerning the selenocompound, the effective amount of the selenocompound must not be administered until after administration of the effective amount of antioxidant protein, preferably of protective selenoprotein, and comprises between 50 and 600 µg/kg of selenium equivalent administered at a cytotoxic concentration so as to reach a plasma concentration of the oxidant selenocompound equal to about 2 to 40 µmol/L, preferably from 10 to 20 µmol/L. The effective amount of selenocompound is the necessary or sufficient amount to reduce hyper-activation of phagocyte cells or neutrophils, and to control hyper-inflammation, the hyper-oxidation state and to stop the chaos situation by a targeted and transient cytotoxic action.

An "ultra-fast" or "flash" administration according to the invention refers to an administration at a rate of more than 2 to 15 mL/sec, preferably from 3 to 10 mL/sec, and more preferably from 4 to 5 mL/sec.

A "repeated flash" or "fractioned" administration corresponds to a succession at short intervals, about 5 to 20 minutes, preferably about 10 minutes, of one to 10, preferably 2 to 5, more preferably 3 flash administrations.

The term "slow administration" according to the invention refers to an amount of selenoprotein administered at a rate of about one quarter to two or five times the total selenoprotein-P of the subject. In particular, the amount of total Sel-P is determined as described in European patent: EP1393078 or U.S. Pat. No. 7,635,491. The administration rate is calculated so that the administration lasts for about 10 min to one hour, preferably about 30 minutes. For example, for a 70 kg man with a plasma volume of about 3000 mL, about 2 to 90 mg of selenoprotein-P in 10 minutes to one hour and preferably in about 30 minutes, namely a rate of 2 to 540 mg/hour, preferably 50 to 400 mg/hour, more preferably from 80 to 200 mg/hour. The amount of total selenoprotein-P varies depending on the subject, and the practitioner will know how to determine the administration rate adapted to each subject. This injection can be repeated from one to three times during the day, particularly the first day every 4, 6, 8 or 12 hours (namely one to four administrations/day of treatment).

"About", in front of a number, means plus or minus 20% of the nominal value of this number.

"subject", according to the present invention, refers to a mammal or a bird. The mammal can be a human (patient), a non-human primate, mouse, rat, dog, cat, horse, or cow, but is not limited to these examples. A subject can be male or female. A subject can be an adult, a child or an infant. A subject is a patient diagnosed with a syndrome, particularly sepsis, or a disease, particularly leukemia. A subject according to the invention can also be an organ or a graft.

The term "sepsis" corresponds to the 2016 definition of sepsis and is defined as an organ dysfunction threatening life and caused by a deregulated response to an infection. The organ dysfunction can be evaluated by an increase in the SOFA of 2 points (or more) that is associated with a death rate of more than 10%. The term "septic shock" must be defined as subjects in sepsis in which there is a particularly pronounced circulatory failure, with cellular and metabolic anomalies that are associated with a higher mortality than in sepsis alone (Singer M and JAMA. 2016; 315(8):801-810).

DETAILED DESCRIPTION

Thus, in a first aspect, the invention relates to a kit comprising: a first container comprising a composition comprising an antioxidant protein, preferably a selenoprotein; and at least one second container comprising at least one composition comprising at least one oxidant compound, preferably a selenocompound.

According to one embodiment, the antioxidant selenoprotein is selected from the group comprising or consisting of: selenoprotein P, glutathione peroxidase, thioredoxin reductase, iodothyronine deiodinase, formate dehydrogenase, methionine sulfoxide reductase, selenophosphate synthetase, selenoprotein Pa (SelPa), selenoprotein W (SelW), selenoprotein T (SelT), selenoprotein R (SelR or SelX), 15 kDa selenoprotein (Sel15), selenoprotein N (SelN), selenoprotein T (SelT2), selenoprotein M (SelM), G-rich selenoprotein (G-rich), selenoprotein W2 (SelW2), selenoprotein BthD (BthD), selenoprotein H (SelH), selenoprotein I (SelI), selenoprotein K (SelK), selenoprotein O (SelO), selenoprotein R (SelR), selenoprotein S (SelS) and selenoprotein Pb (SelPb). According to one embodiment, the composition of the first container comprises a selenoprotein as described hereinabove, in association with any pharmaceutically acceptable excipient. In one embodiment, the antioxidant selenoprotein is selenoprotein P in its complete form or in truncated forms, in a 51 kDa isoform or a 61 kDa isoform, of human origin or of another mammal or bird, or a glutathione peroxidase, among which plasma glutathione peroxidase. In one embodiment, the first container further comprises proteins from the group of heparin-binding proteins (HBP), preferably antithrombin III (AT III).

According to one embodiment, the oxidant selenocompound is selected from the group comprising or consisting of: sodium selenite, selenodiglutathione, selenomethyl selenocysteine, dimethyl selinoxide, selenocystamine, or derivatives of chemical synthesis containing one or several selenium atoms, a hybrid selenium, selenium fluoride salt, selenium chloride salt, selenium bromide salt, selenium iodide salt, a selenoxide, a selenium sulfide salt, selenium telluride salt, selenium potassium salt, selenium germanium salt, selenium barium salt, selenium lead salt, selenium zinc salt or a nitrogenated selenium salt, antimony (III) selenide ($Sb_2Se_3$), arsenic (III) selenide ($AS_2Se_3$), bismuth (III) selenide ($Bi_2Se_3$), cadmium selenide (CdSe), cobalt (II) selenide (CoSe), mercury (II) selenide (HgSe), selenium oxychloride, selenyl chloride ($Cl_2OSe$), selenium sulfide, selenium disulfide ($SeS_2$), silver (I) selenide ($Ag_2Se$), indium (III) selenide ($In_2Se_3$), strontium selenide (SeSr), selenic acid ($H_2O_4Se$), selenium dioxide ($O_2Se$), selenium (Se), selenous acid, selenous acid ($H_2O_3Se$), selenoglutathione.

According to another embodiment, the oxidant selenocompound is a methyl derivative of selenium. According to another embodiment, the oxidant selenocompound is an amino acid containing selenium. According to another embodiment, the oxidant selenocompound is a seleno organic compound (containing selenium) from the group of seleno organic compounds comprising but not limited to alkyl, alicyclic, cyclane, terpenic, aromatic and heterocyclic compounds, in particular selenium methionine, selenourea, or selenium diethyldithiocarbamate.

According to another embodiment, the oxidant selenocompound is a hybrid selenium with formula $Se(x)H(y)$ in which x and y are independently integers comprised between 1 and 10, preferably x is 1 and y is 2.

According to one embodiment, the oxidant selenocompound is sodium selenite ($Na_2SeO_3$), preferably in a nonpentahydrated form. According to one embodiment, the selenocompound is selenocysteine.

According to one embodiment, the composition of the second container comprises an oxidant selenocompound as described hereinabove, in association with any pharmaceutically acceptable excipient.

According to another embodiment, the kit according to the invention comprises a third antioxidant container comprising vitamin C at low dose (antioxidant), vitamin E, a precursor of glutathione, iron salts, gold salts, copper salts at low dose (antioxidant), and/or zinc salts.

According to another embodiment, the kit according to the invention comprises a fourth oxidant container comprising vitamin C at high dose (oxidant dose, greater than 20 mg), iron salts, gold salts, copper salts at high dose, and/or tellurium compounds.

In one embodiment, the kit according to the invention comprises:
a. a first container, comprising a composition comprising an antioxidant protein, preferably a selenoprotein;
b. one, two or at least three second containers, each of the second containers comprising at least one composition comprising at least one oxidant compound, preferably a selenocompound, preferably sodium selenite or selenocysteine; in one embodiment, all the second containers comprise the same composition;
c. optionally at least one third container of oxidant compounds comprising vitamin C, vitamin E, a precursor of glutathione, zinc salts, arsenic salts, copper salts (at low concentration) and/or proteins from the group of heparin-binding proteins (HBP), preferably vitamin E;
d. optionally at least one fourth container of antioxidant compounds comprising vitamin C at high concentration (greater than 20 mg/L), iron salts, gold salts, copper salts, and/or tellurium compounds.

According to one embodiment, a container is one dose unit. Preferably, the first container containing an antioxidant protein, preferably a selenoprotein, has a capacity of 5 to 100 mL, preferably 20 to 50 mL. Preferably, the second container containing the selenocompound has a capacity of 0.05 to 10 mL, preferably 4 mL.

In one embodiment, the composition included in the first or the second container includes at least one pharmaceutically acceptable excipient. Pharmaceutically acceptable excipients according to the invention comprise water, physiological serum, Ringer's solution, a dextrose solution and ethanol solutions, glucose, saccharose, dextran, mannose, mannitol, sorbitol, polyethylene glycol (PEG), phosphate, acetate, gelatine, collagen oils, Carbopol®, vegetables and analogues. Additionally, appropriate preservatives, stabilizers, antioxidants, antimicrobial agents and buffer agents, such as, for example, butylated hydroxyanisole (BHA), butylated hydroxytoluene (BHT), citric acid, tetracycline, and similar can be included.

Other examples of pharmaceutically acceptable excipients that can be used in the invention comprise, but are not limited to, ion exchangers, alumina, aluminium stearate, lecithin, serum proteins such as human serum albumin, buffer substances such as phosphates, glycine, sorbic acid, potassium sorbate, mixtures of partial glycerides of saturated vegetable fatty acids, water, salts or electrolytes, such as protamine sulfate, disodium hydrogenophosphate, potassium hydrogenophosphate, sodium chloride, zinc salts, colloidal silica, magnesium trisilicate, polyvinylpyrrolidone, cellulose-based substances, sodium carboxymethyl cellulose, polyacrylates, waxes, polymers polyethylene polyoxypropylene sequences, polyethylene glycol and wool grease.

Other examples of pharmaceutically acceptable excipients that can be used in the invention comprise, but are not limited to, surfactants (for example hydroxypropylcellulose); appropriate supports, such as, for example, solvents and dispersion media containing, for example, water, ethanol, a polyol (for example glycerol, propylene glycol and liquid polyethylene glycol, and analogues), appropriate mixtures thereof, and vegetable oils, such as, for example, peanut oil and sesame oil; isotonic agents, such as, for example, sugars or sodium chloride; coating agents, such as, for example, lecithin; absorption delaying agents, such as, for example, aluminium monostearate or gelatin; preservatives, such as, for example, benzalkonium chloride, benzethonium chloride, chlorobutanol, thimerosal and analogues; buffers, such as, for example, boric acid, sodium or potassium bicarbonate, sodium or potassium borates, sodium or potassium carbonates, sodium acetate, sodium diphosphate and analogues; tonicity agents, such as, for example, dextran 40, dextran 70, dextrose, glycerin, potassium chloride, propylene glycol, sodium chloride; antioxidants and stabilizers, such as, for example, sodium bisulfite, sodium metabisulfite, sodium thiosulfite, thiocarbamide and analogues; non-ionic wetting agents or clarifying agents, such as, for example, polysorbate 80, polysorbate 20, poloxamer 282 and tyloxapol; viscosity modifying agents, such as, for example, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; and analogues.

According to one embodiment, compositions included in the kit according to the invention are suitable for administration by injection, such as, for example, intravenous, intrathecal, intradermal, intramuscular or epidural injection. In one embodiment, the administration is intravenous. In another embodiment, the kit is suitable for intravenous administration, preferably peripheral. In another embodiment, the kit is suitable for administration by a central venous catheter (for example through the jugular, subclavian or femoral vein), by an arterial catheter for a local effect or in a chaos situation. According to one embodiment of the invention, the compositions included in the kit of the invention are suitable for administration preferably by a multilumen central catheter so as to prevent reactions with other medicines.

According to another embodiment of the invention, the catheter used is a catheter impregnated with antiseptic and/or antibiotic.

According to one embodiment, the compositions included in the kit according to the invention are suitable for administration by injection in an extracorporeal circulation device.

Examples of formulations suitable for administration by injection include, but are not limited to, an injectable solution or an injectable emulsion (such as, for example, an oil-in-water emulsion, a water-in-oil emulsion, an anhydrous emulsion, a solid emulsion or a microemulsion).

In a second aspect, the invention relates to the kit as described hereinabove, for use in a method of sequential administration, to a subject in need thereof, said subject possibly being a patient, of the compositions included in the different containers of the kit. This method is described below.

In a third aspect, the invention relates to a method for sequential administration of the compositions contained in the kit of the invention, to a subject in need thereof, of a therapeutically effective amount of the compositions included in the different containers of the kit described hereinabove, according to a sequential method, namely first the administration of an effective amount of the composition of the first container, namely a composition comprising an antioxidant protein, preferably a selenoprotein, continuously, then the flash administration of an effective amount of the composition of the second container, namely a composition comprising an oxidant selenocompound. In one embodiment, the flash administration of the composition of the second container is an administration in flashes repeated one to five times. In one embodiment, the flash administration of the composition consists in three successive flash administrations of the composition of the second container.

In a fourth aspect, the invention relates to a method for the sequential administration of the compositions contained in the kit of the invention, to a subject in need thereof, of a therapeutically effective amount of the compositions included in the different containers of the kit described hereinabove, according to a sequential method, namely first the administration of an effective amount of the composition of the first container, namely a composition comprising an antioxidant protein, preferably a selenoprotein, continuously, optionally completed by the administration of the composition of the third container, then the flash administration of an effective amount of the composition of the second container, optionally completed by the administration of the composition of the fourth container. In one embodiment, the flash administration of the composition of the second container is an administration in flashes repeated one to five times. In one embodiment, the flash administration of the composition consists in three successive flash administrations of the composition of the second container.

According to another embodiment, the method of the invention comprises a preliminary step of determining the appropriate moment to begin the administration of the compositions contained in the kit of the invention. According to one embodiment, the administration according to the invention begins early before lesions of the endothelium and after the beginning of hyper-inflammation. According to another embodiment, the determination of the appropriate moment to begin administration comprises the detection and quantification of Sel-P in the plasma of a subject. In one embodiment, the beginning of the treatment is decided upon when the subject displays a plasma reduction from half to three-quarters of the reference level of Sel-P, which is about 5 mg/L: in other words, if the subject has a plasma concentration of Sel-P from 1 to 2.5 mg/L, the beginning of treatment can be decided upon. In particular, determining the amount of Sel P is described in European patent: EP 1 393 078 or U.S. Pat. No. 7,635,491, incorporated herein by reference. The increase in lactate is also a good indicator for the beginning of the treatment.

According to one embodiment of the invention, the antioxidant selenoprotein according to the invention must be or is administered to the subject in an amount susceptible of restoring it to the plasma mean level in human. The plasma concentration of Sel-P in human is indeed about 5 mg/L. To restore a normal level of plasma Sel-P nearing about 5 mg/L in a subject suffering from sepsis or systemic acute inflammation for example, the amount of selenoprotein-P administered is, in one embodiment, from 2 to 90 mg, preferably 2 to 30 mg, very preferably 4 to 30 mg of selenoprotein-P slowly administered, i.e., over about 10 min to about one hour, and preferably about 30 minutes. According to another embodiment of the invention, the selenoprotein according to the invention must be or is administered to the subject 1, 2, 3, 4, 5 or 6 times per day for 1, 2, 3 or 4 days, preferably for 3 days.

According to another embodiment, the selenocompound must be or is flash administered so as to obtain a concentration of the selenium element in the plasma of about 2 to 40 µmol/L, preferably from 10 to 20 µmol/L. According to one embodiment, the flash administration is the injection of a composition of selenocompound, preferably sodium selenite or selenocysteine, with a concentration from 0.1 mg/mL to 10 mg/mL, preferably from 0.2 to 5 mg/mL or according to another embodiment about 1.5 mg/mL to 30 mg/mL, preferably 5 mg/mL to 15 mg/mL, expressed in selenium equivalent, in a time of about 0.1 to 4 seconds, preferably about 0.5 to 1 second. According to one particular embodiment, the concentration of flash administered selenium equivalent is about 0.05 to about 0.6 mg/kg of bodyweight, preferably 0.05 to about 0.3 mg/kg of bodyweight, very preferably about 0.1 to 1 mg/kg, about 0.2 to 0.5 mg/kg, preferably about 0.25 to 0.35 mg/kg, preferably about 0.23 mg/kg.

The injection rate is preferably about 1 to 10 mL/sec or 2 to 10 mL/sec, preferably about 3 to 4 mL/sec or 4 to 5 mL/sec. The administration can be made by central catheter or intravenous administration.

According to one embodiment, the therapeutic regimen lasts for several days, preferably 1, 2, 3 or 4 days and the composition comprising the antioxidant protein, preferably the selenoprotein, is administered every 4, 6, 8 or 12 hours, continuously during 10 minutes to 1 hour, said administration being followed, between 10 min and two hours (preferably 10 to 20 minutes) after the end of administration of the selenoprotein, by one to three flashes of the composition comprising the oxidant selenocompound, the flashes being made with intervals of 5 to 20 minutes between them. According to one embodiment, the composition comprising the antioxidant protein, preferably a selenoprotein, is administered during 30 minutes, then after a waiting time of 10 minutes, the composition comprising the selenocompound is administered in three flash injections at intervals of 10 minutes; the complete process is repeated after 4, 6, 8 and/or 12 h.

In one embodiment, the content of the third container (preferably vitamin E) is administered continuously before the administration of flashes of the composition comprising the selenocompound(s), preferably over 10 minutes to 2 h, preferably during the administration of the selenoprotein composition.

In one embodiment, the content of the fourth container (preferably vitamin C at a high concentration) is administered continuously beginning during the time period of administration of the flashes of selenocompounds, and preferably during 10 minutes to 2 h.

According to one embodiment of the invention, the administration can be repeated, with iterative injections followed by rinsing with a neutral solution such as physiological serum or glucose, in accordance with the methods used for injections of contrast products when making scans. This administration method with flash injections allows to obtain cytotoxic concentrations, particularly on hyperactivated inflammatory cells, neutrophils and thus the therapeutic effect by limiting the amount of administered product and therefore its toxicity, particularly pulmonary and/or cardiac.

The flash administration, mimicking a fast injector of the type used in imaging, was chosen to optimize the cytotoxic concentration peak of the selenocompound according to the invention. Furthermore, the repetition of doses at short intervals or fractioned administration, made it possible to optimize the cytotoxic effect on hyperactivated phagocyte cells and the prior administration of selenoprotein-P to protect the endothelium. Furthermore, the total dose administered over three flash injections is much higher than that administered up to the present time. The dose thus fractioned hence allows to obtain very high transient and repeated peaks of the active product while limiting the risk of pulmonary and/or cardiac toxicity.

In one embodiment, the oxidant selenocompound of the second container is included in a transport means or vectorized to target phagocyte cells or the innate response cells. According to one embodiment, the oxidant selenocompound is vectorized or included in a transport means to target in particular circulating immature neutrophils. According to another embodiment, the oxidant selenocompound included in a transport means or vectorized according to the invention expresses specific receptors of phagocyte cells or of the innate response, such as, for example, the CD64, CD36 receptor. According to another embodiment, the oxidant selenocompound included in a transport means or vectorized, expresses specific receptors of circulating immature neutrophils or of cancer cells or of bacteria or of viruses or of parasites or of fungal agents.

According to another embodiment, the transport means according to the invention is a ghost red blood cell. Preparation of ghost red blood cells is described in Dodge J T et al. Arch Biochem Biophys. 1963 January; 100: 119-30; Shaillender M. et al. International Journal of Pharmaceutics 415 (2011) 211-217. The ghost red blood cell is used as a transport and presentation means of the selenocompound; it allows to avoid systemic secondary effects of oxidant selenocompounds for which the severity is known (lethal); it also makes it possible to act at very high concentrations of the selenocompound at the level of the target cells, namely phagocyte cells and more particularly circulating immature neutrophils in the microcirculation and to directly and indirectly protect the endothelium while reducing hyperactivation, cancer cells, bacteria, viruses or parasites or fungal agents.

Within the target cell, the preferred targets are the mitochondria to reduce the activation of hyperactivated granulocytes or other hyperactive cells or the nucleus so as to block the binding of NFκB on DNA and therefore to limit or block the systemic inflammatory reaction.

According to another embodiment, the transport means or vector according to the invention is a nanoparticle. Examples of nanoparticles according to the invention are described in the paper by Vergaro V. et al. Drug-loaded polyelectrolyte microcapsules for sustained targeting of cancer cells. Adv Drug Deliv Rev. 2011 Aug. 14; 63(9): 847-64. For example, the nanoparticles according to the invention include, but are not limited to, a solid lipid nanoparticle, a nanostructured lipid carrier, a dendrimer, a magnetic nanoparticle, a fullerene, a carbon nanotube, a halloysite nanotube, a colloid, a colloid coated with polyelectrolytes, a nanocolloid, polyelectrolyte microcapsules.

According to another embodiment, the transport means or vector according to the invention is a capsule. Preferably, the capsule according to the invention is a capsular bag.

According to one embodiment, the transport means or vector according to the invention is a liposome. According to one embodiment, the vector according to the invention is a cationic liposome. Liposomes known to the person skilled in the art in the subject include, but are not limited to, RPR209120/DOPE. According to another embodiment, the vector according to the invention is a mannosylated cationic liposome to specifically target neutrophils. Liposomes capable of targeting neutrophils are described for example in Kelly C. et al. (Targeted liposomal drug delivery to monocytes and macrophages. J Drug Deliv. 2011; 2011: 727241). Formulations to target phagocytes are well known to the person skilled in the art.

According to another embodiment, the subject of the invention is suffering from a cancer, particularly leukemia, lymphoma or a solid tumor cancer. In one particular embodiment, the subject is suffering from leukemia or lymphoma. Examples of leukemia include, but are not limited to, acute leukemia, chronic leukemia, leukemia of the lymphoid lineage, leukemia of the myeloid lineage, acute lymphoblastic leukemia, chronic lymphoid leukemia, acute myeloblastic leukemia, chronic myeloid leukemia. Examples of lymphomas include, but are not limited to, Hodgkin's and Non-Hodgkin's lymphomas.

According to one embodiment, the subject is suffering from a solid tumor. Solid tumors include carcinomas and sarcomas. Examples of carcinomas include, but are not limited to, cancers of the breast, the lungs, the prostate, the intestine. Examples of sarcomas include, but are not limited to, cancers of the bone, the cartilage.

The present invention also relates to a device adapted to a two-phase administration mode of the kit according to the invention.

According to one embodiment, the device comprises a flash administration mode.

According to another embodiment, the device comprises a slow administration mode.

The administration device cannot be implemented with the infusion pumps usually used and requires an injection at a very high pressure level up to 8 bar and allowing for injection up to 10 mL/seconds. In large mammals and especially in humans, the device comprises an automated high pressure pump of the type used in imaging, allowing very high flows, particularly in central catheters.

According to another embodiment, the device comprises an extracorporeal circulation device. Preferably, this extracorporeal circulation device allows reaching the formed elements of the blood without toxicity for the endothelium.

According to one embodiment, the device according to the invention provides an energy source to generate a fluid pressure and/or flow, while offering the user touch sensitive and/or audible feedback of the generated fluid pressure, allowing the user to modulate the fluid pressure and/or flow. The injection system according to the present invention is capable of supplying both a mode of precise administration at low flow and/or low pressure and also a mode of administration at high flow and/or high pressure.

According to one embodiment, the injection system according to the invention comprises a fluid control module in active liaison with an injector connected to a syringe. The syringe is in fluid connection with an automatic valve of the fluid control module, that is also in fluid communication with a source of contrast through an intermediate flow chamber. The drip chamber preferably comprises a mechanism for detection of the fluid level. A valve, preferably automated, is also in communication with a first inlet orifice of a slot of a pressure isolating valve. The valve prevents saline and/or contaminated fluids from entering into the syringe and allows the control module to quickly stop the fluid flow from the syringe at any pressure and/or any flow. This ability to immediately stop the injection fluid flow at any pressure and any flow significantly eliminates the effects of the conformity of the system and allows both a slow administration of a compound and a flash administration of another compound.

The invention also relates to a kit as described hereinabove, for use in the treatment of sepsis and/or acute systemic inflammation (SIRS, systemic inflammatory response syndrome), severe sepsis, septic shock, a cancer (particularly leukemia, lymphoma or cancer with solid tumor), said use implementing the administration method described hereinabove. In one embodiment, the subject being treated may be in a state of septic shock. In one embodiment, the subject being treated may be in a state of multi-organ failure.

The present invention concerns particularly a kit for use in the treatment of sepsis and/or acute systemic inflammation (SIRS, systemic inflammatory response syndrome) comprising on one hand an antioxidant selenoprotein, and on the other hand a selenocompound, the antioxidant selenoprotein being intended to be administered slowly before the administration of the selenocompound, that is intended to be administered ultra-rapidly after the selenoprotein, preferably in repeated flashes.

The terms sepsis and SIRS as used in the invention can correspond to a septic shock and SIRS conditions giving similar situations requiring the use of catecholamines after filling or during the fast filling phase in the case of very sudden aggravation. Severe sepsis can be shown by the presence of one or several dysfunctions or failures of organs and signs of peripheral hypo-perfusion. Severe sepsis corresponds to a systemic inflammatory response to an infection associated with an organ failure, a hypo-perfusion or hypotension including lactic acidosis, oliguria or an alteration of the mental status. Septic shock can be revealed by the presence of a persistent hypotension despite suitable filling. Adequate generally means filling of 20 to 30 mg/kg. The septic shock is frequently characterized by a systemic inflammatory response to an infection associated with a collapse (hypotension) lasting for more than one hour despite suitable filling and in the absence of other cause of hypotension. (Hypotension occurs later in children and other signs must be considered in pediatrics). Hypotension is defined as a: systolic arterial pressure <90 mmHg, average arterial pressure <60 mmHg, or reduction >40 mmHg in adults or +/−2 SD below the reference one in children).

Severe sepsis, like septic shock, is a syndrome based on the clinical refection of the failure(s) of organ(s), itself or themselves the consequence of the metabolic response to the aggression.

The systemic inflammatory response (SIRS) is a descriptive term used to describe the presence of a systemic inflammatory response independently of its cause, and is recognized by a set of complex signs. According to the latest consensus conference, according to the "2001 SCCM/ESICM/ACCP/ATS/SIS International Sepsis Definitions Conference", these signs are currently defined as follows:

General parameters:
  Fever or hypothermia (<36 or >38.3° C.),
  Tachycardia >90 bpm (beats per minute) or +/−2 standard deviations (SD) from the reference value for the age,
  Tachypnea >30 bpm,
  Mental status disorder,
  Edema or positive water sodium balance (>20 ml/kg over 24 h).
Inflammatory parameters:
  Hyperleukocytosis or leukopenia (>12,000 or <4000/µl),
  Presence of >10% of immature forms,
  Plasma C reactive Protein (CRP)+/−2 SD from reference values,
  Plasma procalcitonin (PCT)+/−3 SD from reference values,
Hemodynamic parameters:
  Arterial hypotension (systolic arterial pressure <90 mmHg, average arterial pressure,
  <70 mmHg, or reduction >40 mmHg in adults or +/−2 SD below the reference one in children).
  Mixed venous blood oxygen saturation ($SvO_2$) >70% (cannot be used for children),
  Cardiac index >3.5 L/min·m$^2$ (cannot be used for children).
Organ dysfunction:
  Arterial hypoxemia ($PaO_2/FiO_2$<300),
  Oliguria (acute) (diuresis <0.5 ml/kg/h or 45 ml during the last 2 hours),
  Increase in creatinine ≥0.5 mg/dl,
  Coagulation abnormalities (activated thromboplastin time >60 s or >1.5 of the international normalized percentage),
  Ileus (abdominal silence during the examination),
  Thrombocytopenia <100 000/µl,
  Hyperbilirubinemia (total bilirubinemia >4 mg/dl or 70 mmol/L).
Tissue perfusion parameters:
  Hyperlactatemia >3 mmol/L,
  Increase in the capillary reperfusion time, The term multi-organ failure as used in the invention corresponds to a clinical syndrome characterized by an acute and potentially reversible dysfunction of an organ or a major function, not directly involved in the initial pathological process. Multi-organ failure is generally associated with a hypotension (systolic arterial pressure <90 mmHg or reduction >40 mmHg starting from the initial value in the absence of other causes).

Multi-organ failures are readily based on the SOFA (Sepsis Related Organ Failure Assessment) score (Table 1), the first two grades are associated with dysfunctions, the last two with failures. They are then most often associated with the requirement to implement life-support substitution to keep the subject alive. This may include in particular (i) ventilation by an appliance to assist breathing, (ii) perfusion and administration of catecholamines to maintain a satisfactory pressure and a good blood flow, (iii) dialysis to replace the kidneys, (iv) blood and platelet transfusion. These substitutions and their monitoring, will have a major impact on the cost of treatment for the subjects in a state of septic shock.

TABLE 1

(SOFA score from 0 to 20) (Dopa for Dopamine, Adre for Adrenalin, Noradre for Noradrenalin, diu for diuresis in ml/d) The SOFA (Sepsis Related Organ Failure Assessment) score is one of the most frequently used failure scores.

| Functions | No failure (0) | 1 | 2 | 3 | 4 |
|---|---|---|---|---|---|
| Respiratory ($PaO_2/FiO_2$ in mmHg) | >400 | <400 | <300 | <200 and ventilated | <100 and ventilated |
| Coagulation (platelets in $10^3/mm^3$) | >150. | <150 | <100 | <50 | <20 |
| Hepatic (bilirubin in μmol/L) | <20 | >20 | >33 | >102 | >204 |
| Cardiovascular (Average arterial pressure) | >70 | <70 | Dopamine ≤ 5 or Dobutamine | Dopa > 5 Adre. or Noradre. ≤ 0.1 | Dopa > 15 Adre. or Noradre. > 0.1 |
| Central nervous system (Glasgow score) | 15 | 13-14 | 10-12 | 6-9 | <6 |
| Renal (Creatinine) | <110 | >110 | >171 | >300 or diu < 500 | >440 or diu < 200 |

The definition of sepsis was modified in 2016 and is defined as an organ dysfunction threatening life and caused by a deregulated response to an infection. The organ dysfunction can be evaluated by an increase in the SOFA of 2 points (or more) that is associated with a mortality of more than 10%. Septic shock must be defined as subjects in sepsis for which there is a particularly pronounced circulatory failure, with cellular and metabolic anomalies that are associated with a higher mortality than in sepsis alone (Singer M and JAMA. 2016; 315(8):801-810).

Markers allowing to monitor the evolution of a sepsis are known to person skilled in the art. The plasma concentration of lactate and its evolution is a delayed but frequently used marker of the occurrence of a sepsis and of the monitoring of the efficiency of care of a septic shock (or a severe sepsis). Other recognized markers are those of the monitoring of organ dysfunctions such as those listed in the 2001 consensus conference and in the SOFA score. Other markers, such as nitrogen oxide NO, cytokines, growth factors particularly of the endothelium, microparticles, measuring of receptors, are used but in the context of research. The measuring of selenoprotein-P was proposed as an early marker of sepsis and its severity.

According to one embodiment, the subject of the invention is a subject suffering from sepsis and/or acute systemic inflammation.

According to another embodiment, the subject of the invention is suffering from sepsis in the early phase.

According to one embodiment, the subject of the invention is a subject who has experienced a cardiac arrest or ischemia reperfusion.

According to one embodiment, the subject of the invention is under antibiotic treatment or is suffering from a bacterial infection, in particular resistant to antibiotics or is suffering from a viral infection.

According to one embodiment, the subject of the invention is an organ and the method according to the invention is implemented before the organ removal in the context of a graft preparation, in the context of a graft and/or in the context of a graft rejection.

Pre-existing pathologies may increase the risk incurred by the subject to develop a sepsis (according to the definition of the document, severe sepsis and septic shock) during an infection: an alcoholic liver disease, a cirrhosis, anorexia, undernutrition, malnutrition, a diabetes, a cancer, a blood disease, a system disease, a subject suffering from acquired immune deficiency syndrome (AIDS) or a chronic inflammatory pathology, in particular intestinal, and the recent prior occurrence of a sepsis episode, the presence of a large number of catheters. According to one embodiment, the subject of the invention is suffering from one of these pathologies.

Acute inflammation is also a major event in irradiation victims who do not die immediately. It also relates to acute respiratory distress syndromes by exposure to suffocating, blistering and irritating gases, and other organ damages by acute inflammation. Furthermore, acute inflammation is a secondary event following exposure to weapons of electromagnetic waves effect.

Acute inflammation also refers to states of allergic shock or severe forms of allergies such as "Quincke's edema".

Acute inflammation is also the consequence of a late revascularization reversal of an acute ischemia regardless of the territory (cerebral, cardiac, lower limbs), crush syndrome, revascularization after cardiac arrest, severe acute infected or non-infected pancreatitis, a neuro-malaria (pernicious access), acute flare of lymphoma or of vasculitis.

Acute inflammation also concerns the consequences of the immune system failure during nosocomial infections with increasingly opportunist pathogens.

According to another embodiment, the subject of the invention is suffering from severe sepsis. A severe sepsis in the meaning of the present invention is a sepsis with acute dysfunction of one or several organs ("multi-organ failure").

According to another embodiment, the subject of the invention is suffering from a septic shock.

According to one embodiment, the subject of the invention is an apparently healthy subject, which means that the subject has not been previously diagnosed or identified as having or suffering from a septic state, or is in the process of developing a septic state or SIRS with similar severity.

According to one embodiment, the subject may be a subject asymptomatic of a septic state. As used herein, an "asymptomatic" subject refers to a subject who/that does not present the classical symptoms of a septic state.

According to another embodiment, the subject may be at risk of having or developing a septic state, as defined by clinical clues such as, for example, ethnic origin, age, a comorbidity, alcohol abuse, poverty, a low socio-economic status, or season (sepsis is more frequent in winter in regions in which it exists).

According to another embodiment, the subject has at least two of the following symptoms: temperature higher than 38.2° C. (or hypothermia lower than 36° C.), tachypnea higher than or equal to 30 movements per minute (min), tachycardia higher than 120 beats per minute, systolic arterial pressure lower than 110 mmHg.

According to another embodiment, the subject has at least two of the following symptoms: temperature higher than 38.2° C. (or hypothermia lower than 36° C.), tachypnea higher than or equal to 22 movements per minute (min), acute confusional state; tachycardia higher than 120 beats per minute, systolic arterial pressure lower than 100 mmHg.

According to one embodiment, the subject is an infant or a child presenting factors conducive to the development of septic states. Factors conducive to the development of a septic state in an infant comprise, but are not limited to, immunocompetence (purpura fulminans), immunodeficiency (congenital or acquired immune system deficiencies), comorbidity (cardiac or urinary malformations), severely burned, polytraumatized, or hospitalized in a resuscitation service.

According to another embodiment, the subject is a child presenting factors conducive to the development of a sepsis. Examples of infections at the origin of a sepsis comprise, but are not limited to, meningitis, septicemia, focal infections, respiratory infections, primitive bacteremia, genito-urinary infections, abdominal infections, infections of the soft tissues, infections of the central nervous system, endocarditis. Examples of focal infections comprise, but are not limited to, pneumonia, otitis, epiglottitis, conjunctivitis, arthritis, urethritis, pericarditis.

According to another embodiment, the subject of the invention presents factors conducive to a fast evolution towards an acute inflammatory reaction that include, in a non-limitative manner: a) sepsis: a septicemia, a pulmonary infection (such as pneumonia), an intra-abdominal infection, a serious infection of purpura, necro-bullous lesions of necrotizing fasciitis, nosocomial infections, peritonitis, meningitis or bacterial septicemia, b) SIRS, a pancreatitis, an extensive burn, severe acute asthma, polytrauma, a massive irradiation, severe acute asthma, smokes from fire, irritating gases (combat), ischemia reperfusion as in crush syndromes and molecular excitations of non-lethal weapons.

According to another embodiment, the subject of the invention has undergone a major surgical operation, a surgical operation with clamping (ischemia-reperfusion), a surgical operation with extra-corporeal circulation.

Thus, one object of the invention is a method according to the invention, wherein the subject is a patient suffering from sepsis and/or acute systemic inflammation and/or sepsis in the early stage, and/or a severe sepsis, and/or a septic shock and/or multiple organ failures, and/or has at least two of the following symptoms: temperature higher than 38.2° C. (or hypothermia lower than 36° C.), tachypnea higher than or equal to 30 movements per minute (min), preferably higher than or equal to 22 movements per minute (min), (tachycardia higher than 120 beats per minute), systolic arterial pressure lower than 100 mmHg, acute confusional state; and/or is a subject, in particular an infant or a child presenting factors conducive to the development of septic states or sepsis or factors conducive to a fast evolution towards an acute inflammatory reaction, has undergone a major surgical operation, a surgical operation with clamping (ischemia-reperfusion) or extra-corporeal circulation.

In a fifth aspect, the invention relates to a kit as described hereinabove for use in the treatment of cancers. According to one embodiment, the invention relates to a kit as described hereinabove for use in the treatment of leukemia, preferably acute forms of leukemia, said use implementing the method of administration according to the invention described hereinabove. Preferably, the method and the kit according to the invention are used as adjunctive treatment for the treatment of leukemia, preferably acute forms of leukemia. In particular, the kit according to the invention is used as adjunctive treatment particularly during surgery to limit the proliferation of cancer cells, whose means of attachment to the endothelium present similarities with hyperactivated granulocytes.

According to one embodiment, the invention relates to a kit as described hereinabove for use in the treatment of solid tumors.

In a sixth aspect, the invention relates to a kit as described hereinabove, for use to reduce the production of peroxynitrite or other reactive nitro-oxygenated derivatives (e.g., superoxide anion $O_2-$, singlet oxygen $O_2$, hydrogen peroxide $H_2O_2$, or ozone $O_3$) in a subject in need thereof, said use implementing the method of administration according to the invention described hereinabove.

In a seventh aspect, the invention relates to a kit as described hereinabove for use to reduce hyper-inflammation in a subject in need thereof, said use implementing the method of administration according to the invention described hereinabove.

In an eighth aspect, the invention relates to a kit as described hereinabove for use to reduce the quantity of bacteria, or viruses, or parasites, or fungal agent in a subject in need thereof, said use implementing the method of administration according to the invention described hereinabove.

EXAMPLES

Figure 1:
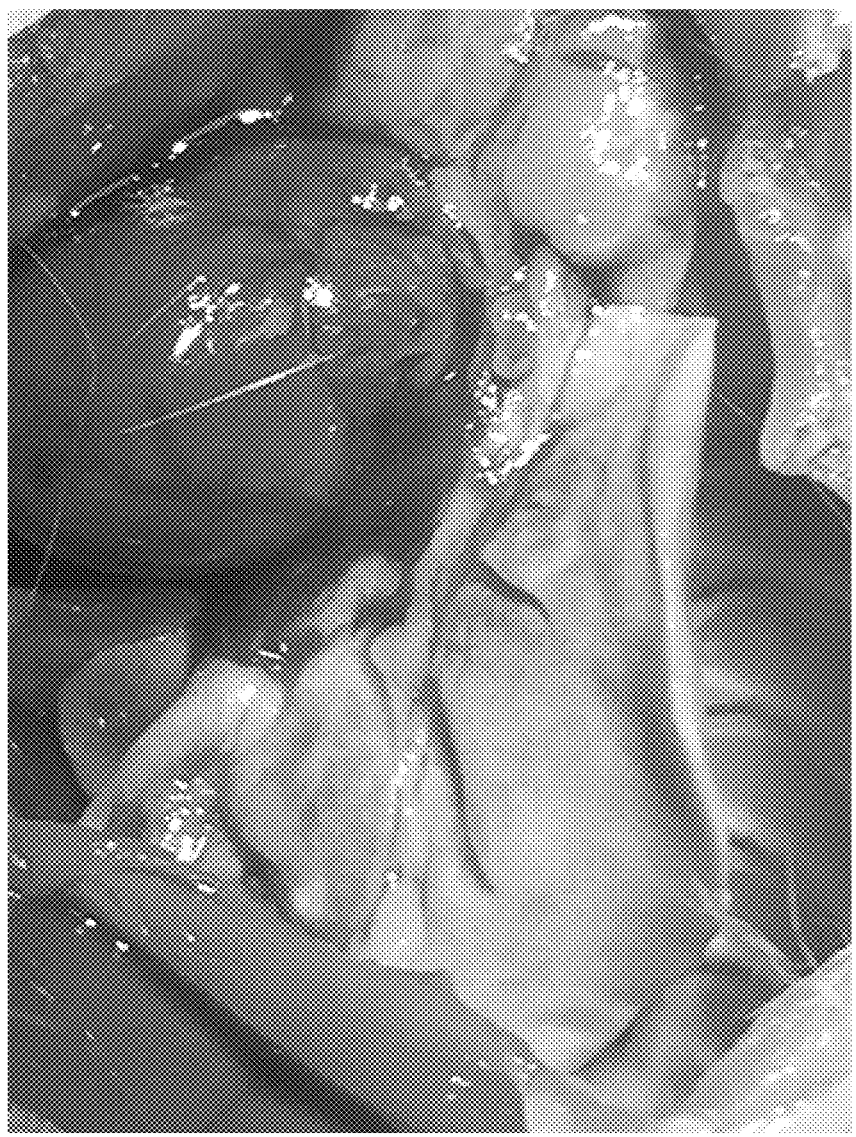
FIG. 1 is a photograph showing the appearance of the lungs of a deceased rat with the complete treatment (Sel P+$Na_2SeO_3$). The appearance of the lungs is sensibly normal.

This invention will be better understood after reading the following examples that illustrate the invention in a non-limitative manner.

Example 1: Composition According to the Invention

Composition A is a solution of oxidant selenocompound: sodium selenite with a concentration of 0.2 mg/ml in Se equivalent.

Composition A2 is a control solution of water for injection (wfi).

Composition B is a solution of plasma proteins enriched in Sel-P and containing 0.05 mg/ml of Sel-P. In one preferred embodiment, this purified solution comprises heparin-binding proteins (HBP) including AT III.

Composition B2 is control solution of 4% albumin diluted to 1:20.

Example 2: Inclusion of the Selenocompound According to the Invention in a Ghost Red Blood Cell In one embodiment, the oxidant selenocompound according to the invention is included in a ghost red blood cell, allowing the liberation of the oxidant selenocompound in the microcirculation and at the specific site of the adhesion of phagocyte cells or cells of the innate immune response with the endothelial cells. This enables a cytotoxic action limiting hyper-inflammation and limiting adhesion of the phagocyte cells or the cells of the innate immune response with the endothelial cells, adhesion that involves disulfide bridges and to directly or indirectly protect the endothelium.

Example 3: Device According to the Invention

The invention also comprises a device according to the invention that administers the selenoprotein (in this example, selenoprotein P) slowly and then the selenocompound (in this example, sodium selenite) in flash.

For example, the administration device may be the Swiss Medical Care system: Computed Tomography (CT) Express III™ Contrast Media Delivery System (CMDS), or CT Premica™ CMDS described in patent applications: EP1713528, EP2298382, EP2477677.

For example, the administration device may also be the Medrad Inc. system described in international application: WO2005104687, or application US2004242996.

Example 4: Kit According to the Invention

The kit according to the invention comprises at least two distinct containers, one containing compound A and the other containing compound B:

Container of composition A: 0.15 ml of a solution of sodium selenite with a concentration of 0.2 mg/ml in Selenium (Se) equivalent.

Container of composition B: 1 mL of a plasma solution enriched in Sel-P at a concentration of 0.05 mg/mL.

Example 5: Effect of Successive Administrations of Sel-P and $Na_2SeO_3$

Material and Methods
Rats

Care of the animals and experimental procedures were approved by the ethics committee and validated following the procedure in force with the Ministry.

The experiments will be conducted on 12-week old male IOPS Han Ico Wistar rats. (Charles River, L'Arbresle, France). Consequently, the weight of the animals at the time of the experiment is between 380 and 400 g. They will be kept in individual cages made of thermoformed polystyrene in accordance with standards of the Ministry of Agriculture and Environment and kept at a temperature of 21±1° C., with a relative humidity of 55% and a 12 h alternation of the nycthemeral cycle (day/night). They will have free access to an appropriate diet and free access to water corresponding to an adequate input of selenium. A one-week acclimatization will be conducted to limit experimental stress. Animals that are obviously ill at the beginning of the experiments will be excluded.

Animal Groups:
- Group 1: Diseased controls LPS only: no action.
- Group 2: 30-minute perfusion controls: administration of control solution B2 over 30 minutes (min.), 10 min. wait then administration of $Na_2SeO_3$ (A) over 30 min (perfusion).
- Group 3: Compositions B and A controls: administration of control solution B2 over 30 min, 10 min. wait then administration of control solution A2 in 3 flash injections every 10 min.
- Group 4: Action of composition A alone: administration of control solution B2 over 30 min, 10 min wait, then administration of $Na_2SeO_3$ (A) in 3 flash injections every 10 min.
- Group 5: Action of composition B alone: administration of Sel-P (B) over 30 min, 10 min. wait then administration of control solution A2 in 3 flash injections every 10 min.
- Group 6: Action of compositions B and A in synergy: administration of Sel-P (B) over 30 min, 10 min. wait then administration of $Na_2SeO_3$ (A) in 3 flash injections every 10 min.

The main criterion is the plasma concentration of lactate as was mentioned to the ethics committee.

Solutions
- LPS: LPS *Salmonella typhimurium* Serotype LG511, Sigma L-6511 (Batch 12K4090).
- Composition A (sodium selenite): The working solution is at a concentration of 0.2 mg/ml of Se equivalent. Injection at H 3 h40 after the injection of LPS into the internal jugular vein through the central catheter of the amount of working solution to be made between two lines (corresponding to 0.2 mg/ml) so as to deliver 0.1 mg/kg of selenium equivalent in the form of sodium selenite. Perfusion maintained by physiological serum, minimum 0.1 ml/h (NaCl).
- Composition A2: Water for injection (wfi) that will be to inject according to the same procedure and rinsing according to the same procedure.
- Composition B: the solution of human plasma enriched with selenoprotein-P at 0.05 mg/ml, with a purification of about 8% with a protein concentration of 2 g/L. Injection of 2.5 ml in 30 minutes to each animal.
- Composition B2: 4% human albumin to be diluted to 1:20—Injection of 1 ml of the solution diluted to 1:20 to the animals over 30 min at a rate of 2 ml/h.

Experimental Protocol:
- H0: Triggering of the septic shock by the intra-peritoneal administration of LPS at 50 mg/kg at H0. 4 control rats were initially given a dose of 50 mg/kg of LPS.
- H1, the rats are anaesthetized and instrumented. The anesthetic is applied in the form of penthotal and fentanyl, the animals are then tracheostomized and a catheter is put into place in the jugular. Perfusion is maintained by physiological serum, with a minimum of 0.1 ml/h (NaCl).

Operation at H3: Continuous perfusion of Sel-P (B) (1 ml) or control B2 (1 ml) over 30 min. Wait of 10 minutes. Continuous perfusion is maintained to limit losses of composition B (or B2).

Operation at H 3 h40, 3 ultra-fast or flash injections in 0.5 sec of 0.15 ml of composition A (sodium selenite) or composition A2 (control) every 10 min. and rinsing of the perfusion with 0.15 ml of physiological serum. The injection is made directly at the internal jugular catheter.

General anesthesia is maintained by intraperitoneal administration of a half-dose of penthotal every hour or at the first sign of awakening.

Samples Taken at H 6 h30:

Sampling and euthanasia: final sampling and euthanasia at 6 h30 after the injection of LPS, or immediate sampling if the animal dies during the experimental protocol.

Collection of a blood gas sample and collection of a tube of EDTA and lithium heparinate at the time of euthanasia of the rats.

A lung sample was taken, weighed and placed in the freezer in order to be able to determine, at least, the dry/wet ratio as a pulmonary edema indicator.

Measured Parameters:

Immediate measurement of lactate, of gases in venous blood, of the blood ionogram, of glycemia and of the hemoglobin level and of the hematocrit of the creatinine level. Other measurements will be made on the samples frozen on EDTA and lithium heparinate tubes.

Results

Effect of the Treatment on the Lactate Concentration:

Control groups comprise: groups 1; 2 and 4 with sodium selenite in continuous administration or flash administration, group 3 with injection of albumin and injection of water and group 5 with administration of Sel-P.

Animals in group 4 do not survive the administration of sodium selenite alone. Consequently, no value is shown in Table 2.

For the group 6 overall, the lactate concentration is significantly reduced in rats of this group compared to the rats of the control groups. The lactate concentration is 2.28±0.31 vs 6.48±1.88 mmol/L (p=0.017 Mann Whitney test) (Table 2).

This is related to the normalized value of the lactate concentration and to the very small variation between lactate concentrations in this group in a model of very severe LPS (50 mg/kg of LPS) and euthanasia at 6 h30 after the administration of LPS.

Furthermore, the three rats of group 6 (B: selenoprotein-P over 30 minutes and 3 flash injections of A: non-hydrated sodium selenite at a dose of 0.1 mg/kg by flash injection) have biological constants close to the reference values despite the administration 6 h30 earlier of a fatal dose of LPS at 50 mg/kg.

Effect of the Treatment on Blood Gases:

Venous blood gases have been measured in euthanized animals (Table 3).

In group 6: saturation in mixed central venous blood is high which is a sign of the absence or low level of metabolic distress, and of the adapted heart output. Furthermore, glycemia is within the reference values, and the pH is slightly modified. At the kidney level, there is very little increase in the concentration of creatinine.

Furthermore, the macroscopic appearance of the lungs is almost normal, which is very different from the macroscopic appearance in control rats which, in this very severe model, have a hepatized aspect, a sign of a very severe acute respiratory distress syndrome (FIG. 1).

In group 2: the table shows that a rat having received diluted albumin and sodium selenite at a dose of 3×0.1 mg/kg=0.3 mg/kg of selenium over 30 minutes presents very different biological parameters from the group 1 of control rats with very severe, pre-lethal distress: a major increase in lactate is observed, with a lowered pH, a very low glycemia and an increase in creatinine. ScvO$_2$ collapsed probably due to very low heart output imposing to cells a maximum oxygen extraction despite the sepsis situation.

Figure 2:
FIG. 2 is a photograph showing the appearance of the lungs of a rat having received only Sel-P. The appearance of the lungs shows little alteration.

In group 5: an incomplete improvement is observed in rats having only received selenoprotein-P. pH values are lowered and the kidney function is little changed, as is the value of glycemia compared with what is observed in the previous rat (group 2), corresponding to what is observed in most control rats. ScvO$_2$ also remains within values less altered than in the previous rat. There is also a smaller change to the lung appearance which does not have the hepatized aspect observed in control rats (FIG. 2).

TABLE 2

| | Group: | Lactate level |
|---|---|---|
| Controls | 1 | 4.78 |
| | 1 | 3.76 |
| | 1 | 5.45 |
| | 1 | 7.36 |
| | 2 | 8.75 |
| | 3 | 6.78 |
| | 3 | 8.45 |
| Treatment: Sel-P | 5 | 3.35 |
| | 5 | 4.79 |
| Treatment in synergy | 6 | 2.2 |
| | 6 | 2.63 |
| | 6 | 2.02 |

TABLE 3

| Group: | 1 | 1 | 1 | 1 | 2 | 3 | 3 | 5 | 5 | 6 | 6 | 6 |
|---|---|---|---|---|---|---|---|---|---|---|---|---|
| pH | 7.44 | 7.270 | 7.43 | 6.74 | 6.906 | 7.240 | 7.210 | 7.357 | 7.346 | 7.400 | 7.491 | 7.313 |
| PaO$_2$ mmHg | 387 | 33.7 | 40.9 | 59.6 | 16 | 37.9 | 33.7 | 55.3 | 34 | 51.5 | 40.4 | 47.8 |
| PCO$_2$ mmHg | 20.1 | 83.4 | 33.2 | 44.9 | 97 | 39.9 | 56.5 | 44.7 | 45.4 | 48.7 | 34.1 | 54.3 |
| CO$_3$H— | 13.7 | 37.8 | 23.3 | 6.1 | 19.6 | 18.6 | 22.2 | 25.1 | 27.7 | 31 | 26.6 | 28.3 |
| ScvO$_2$ or SaO$_2$ | 100 | 54 | 79.3 | 58.3 | 8.9 | 65 | 51.2 | 86.9 | 64.5 | 85.9 | 80.7 | 79.3 |
| Probable arterial lactate | 4.78 | | 5.45 | 7.36 | | | | | | | | |

TABLE 3-continued

| Group: | 1 | 1 | 1 | 1 | 2 | 3 | 3 | 5 | 5 | 6 | 6 | 6 |
|---|---|---|---|---|---|---|---|---|---|---|---|---|
| Venous lactate | | 3.76 | | | 8.75 | 6.78 | 8.45 | 3.35 | 4.79 | 2.2 | 2.63 | 2.02 |
| Na | 139 | 143 | 141 | 155 | 144 | 105 | 132 | 140 | 143 | 145 | 144 | 142 |
| K | 4.5 | 5.8 | 4.2 | 5 | 7.5 | >12 | 9.9 | 4.6 | 5.2 | 6.4 | 5.2 | 6.1 |
| Cl | 116 | 104 | 105 | 133 | 116 | 81 | 103 | 107 | 105 | 107 | 108 | 106 |
| Ca | 1.01 | 1.16 | 1.08 | 0.62 | 1.21 | 0.57 | 0.71 | 1.12 | 1.17 | 1.12 | 1.14 | 1.22 |
| AgapK | 14 | 7 | 17 | 21 | 16 | ND | 17 | 13 | 16 | 13 | 15 | 14 |
| Ht | 40 | 48 | 38 | <10% | 35 | 45 | 50 | 38 | 41 | 35 | 38 | 35 |
| cHb | 13.5 | 16.4 | 12.9 | NA | 12.1 | 15.4 | 17 | 13 | 14 | 11.8 | 13 | 11.9 |
| Gly | 1.1 | 1.01 | 1.2 | 1.21 | 0.27 | 0.52 | 0.67 | 1.16 | 1.25 | 1.14 | 1.23 | 1 |
| Creat | 77 | 180 | 113 | 44 | 156 | 132 | 215 | 52 | 94 | 100 | 78 | 113 |

The invention claimed is:

1. Method for treating sepsis and/or acute systemic inflammation, solid cancers or leukemia in a subject in need thereof, said method comprising sequentially administering to the subject:
   first a therapeutically effective amount of a composition comprising at least one antioxidant selenoprotein by continuous administration over 10 minutes to 1 hour, wherein the therapeutically effective amount is 2 to 90 mg of the selenoprotein; and
   then a therapeutically effective amount of at least another composition comprising at least one oxidant selenocompound by administration in one flash in a time of 0.1 to 4 seconds or in several repeated flashes in a time of 0.1 to 4 seconds each, wherein the therapeutically effective amount per each administered flash is 0.05 to 0.6 mg of Se equivalent/kg of body weight of the selenocompound.

2. Method according to claim 1, wherein the therapeutically effective amount of the at least another composition comprising at least one oxidant selenocompound is administered to the subject in three repeated flashes.

3. Method according to claim 1, wherein the therapeutically effective amount of the composition comprising at least one antioxidant selenoprotein is administered to the subject by continuous injection of 2 to 90 mg of selenoprotein P in its complete form or in truncated forms over 10 minutes to 1 hour, and wherein the therapeutically effective amount of the at least another composition comprising at least one oxidant selenocompound is administered to the subject 10 to 20 minutes after the end of the first administration by injection of 0.05 to 0.6 mg of Se equivalent/kg of body weight of the selenocompound, the dose being fractioned into 3 successive flash injections, in a time of 0.1 to 4 seconds each, at intervals of 10 minutes.

4. Method according to claim 1, wherein the subject is suffering from sepsis and/or acute systemic inflammation and/or sepsis in the early stage, and/or a severe sepsis, and/or a septic shock and/or multi-organ failures, and/or has at least two of the following symptoms: temperature higher than 38.2° C., hypothermia lower than 36° C., tachypnea higher than or equal to 22 movements per minute, tachycardia higher than 120 beats per minute, or systolic arterial pressure lower than 100 mmHg.

5. Method according to claim 1, wherein the subject is suffering from a solid cancer or leukemia.

6. Method according to claim 1, wherein said method allows to reduce the production of peroxynitrite or to reduce hyper inflammation in the subject in need thereof.

7. Method according to claim 1, wherein the subject is suffering from an acute inflammation or is suffering from an acute respiratory distress syndrome.

8. Method according to claim 1, wherein the subject is suffering from an acute inflammation due to an allergic shock or an allergy; or has experienced a cardiac arrest or an ischemia reperfusion; or is undergoing antibiotic treatment or is suffering from a bacterial infection or a viral infection.

9. Method according to claim 1, wherein said composition comprising at least one antioxidant selenoprotein further comprises a pharmaceutically acceptable excipient and proteins from the group of heparin-binding proteins (HBP).

10. Method according to claim 1, wherein said antioxidant selenoprotein is selected from the group consisting of selenoprotein P, glutathione peroxidase, thioredoxin reductase, iodothyronine deiodinase, formate dehydrogenase, methionine sulfoxide reductase, selenophosphate synthetase, selenoprotein Pa (SelPa), selenoprotein W (SelW), selenoprotein T (SelT), selenoprotein R or selenoprotein X (SelR or SelX), 15 kDa selenoprotein (Sel15), selenoprotein N (SelN), selenoprotein T2 (SelT2), selenoprotein M (SelM), G-rich selenoprotein (G-rich), selenoprotein W2 (SelW2), selenoprotein BthD (BthD), selenoprotein H selenoprotein I (SelI), selenoprotein K (SelK), selenoprotein O (SelO), selenoprotein S (SelS), and selenoprotein Pb (SelPb).

11. Method according to claim 1, wherein said antioxidant selenoprotein is selenoprotein P in its complete form or in truncated forms.

12. Method according to claim 1, wherein said oxidant selenocompound is selected from the group consisting of sodium selenite, selenocysteine, selenodiglutathione, selenomethyl selenocysteine, dimethyl selinoxide, selenocystamine, derivatives of chemical synthesis containing one or several selenium atoms, a hybrid selenium, selenium fluoride salt, selenium chloride salt, selenium bromide salt, selenium iodide salt, a selenoxide, a selenium sulfide salt, selenium telluride salt, selenium potassium salt, selenium germanium salt, selenium barium salt, selenium lead salt, selenium zinc salt or a nitrogenated selenium salt, antimony selenide, arsenic selenide, bismuth selenide, cadmium selenide, cobalt selenide, mercury selenide, selenium oxychloride, selenyl chloride, selenium sulfide, selenium disulfide, silver selenide, indium selenide, strontium selenide, selenic acid, selenium dioxide, selenium, selenous acid, and selenoglutathione.

13. Method according to claim 1, wherein said oxidant selenocompound is sodium selenite or selenocysteine.

14. Method according to claim 1, wherein said oxidant selenocompound is included in a transport means selected from the group consisting of a ghost red blood, a capsule, a nanoparticle, and a liposome.

15. Method according to claim 1, wherein the administration steps are repeated every 4, 6, 8 or 12 hours for at least one day.

* * * * *